(12) United States Patent
Germain et al.

(10) Patent No.: US 9,161,809 B2
(45) Date of Patent: Oct. 20, 2015

(54) SYSTEMS FOR TREATING A VERTEBRAL BODY

(71) Applicant: Dfine, Inc., San Jose, CA (US)

(72) Inventors: Aaron Germain, Campbell, CA (US); Csaba Truckai, Saratoga, CA (US)

(73) Assignee: Dfine, Inc., San Jose, CA (US)

( * ) Notice: Subject to any disclaimer, the term of this patent is extended or adjusted under 35 U.S.C. 154(b) by 0 days.

(21) Appl. No.: 14/312,344

(22) Filed: Jun. 23, 2014

(65) Prior Publication Data

US 2014/0371740 A1 Dec. 18, 2014

Related U.S. Application Data

(63) Continuation of application No. 12/578,455, filed on Oct. 13, 2009, now Pat. No. 8,758,349, and a continuation-in-part of application No. 12/571,174, filed on Sep. 30, 2009, now Pat. No. 8,663,226.

(60) Provisional application No. 61/104,987, filed on Oct. 13, 2008.

(51) Int. Cl.
*A61B 17/00* (2006.01)
*A61B 18/14* (2006.01)
*A61B 17/16* (2006.01)
(Continued)

(52) U.S. Cl.
CPC ......... *A61B 18/1492* (2013.01); *A61B 17/1642* (2013.01); *A61B 17/1659* (2013.01); *A61B 17/1671* (2013.01); *A61B 17/3421* (2013.01); *A61B 17/8805* (2013.01); *A61B 18/1206* (2013.01); *A61B 17/3472* (2013.01); *A61B 2017/003* (2013.01); *A61B 2018/00339* (2013.01); *A61B 2018/00577* (2013.01); *A61B 2018/00589* (2013.01); *A61B 2018/1412* (2013.01); *A61B 2018/1475* (2013.01)

(58) Field of Classification Search
CPC ........... A61B 18/1492; A61B 17/1642; A61B 17/1671; A61B 17/3421; A61B 17/3472; A61B 2017/003; A61B 17/1659; A61B 17/8805; A61B 18/1206; A61B 2018/00339; A61B 2018/00577; A61B 2018/00589; A61B 2018/1475
See application file for complete search history.

(56) References Cited

U.S. PATENT DOCUMENTS 4,411,266 A 10/1983 Cosman
4,456,017 A 6/1984 Miles
(Continued)

FOREIGN PATENT DOCUMENTS

JP 2004-242936 9/2004
WO WO 93/04634 3/1993
(Continued)

*Primary Examiner* — Christopher Beccia
*Assistant Examiner* — Diana S Jones
(74) *Attorney, Agent, or Firm* — Levine Bagade Han LLP

(57) ABSTRACT

Methods and devices that displace bone or other hard tissue to create a cavity in the tissue. Where such methods and devices rely on a driving mechanism for providing moving of the device to form a profile that improves displacement of the tissue. These methods and devices also allow for creating a path or cavity in bone for insertion of bone cement or other filler to treat a fracture or other condition in the bone. The features relating to the methods and devices described herein can be applied in any region of bone or hard tissue where the tissue or bone is displaced to define a bore or cavity instead of being extracted from the body such as during a drilling or ablation procedure.

20 Claims, 20 Drawing Sheets

(51) Int. Cl.
*A61B 17/34* (2006.01)
*A61B 17/88* (2006.01)
*A61B 18/12* (2006.01)
*A61B 18/00* (2006.01)

(56) References Cited

U.S. PATENT DOCUMENTS

| | | | |
|---|---|---|---|
| 4,476,861 A | 10/1984 | Dimakos et al. | |
| 4,595,006 A | 6/1986 | Burke et al. | |
| 5,282,821 A | 2/1994 | Donahue | |
| 5,284,128 A | 2/1994 | Hart | |
| 5,322,505 A | 6/1994 | Krause et al. | |
| 5,449,351 A | 9/1995 | Zohmann | |
| 5,458,597 A | 10/1995 | Edwards et al. | |
| 5,599,346 A | 2/1997 | Edwards et al. | |
| 5,620,447 A | 4/1997 | Smith et al. | |
| 5,628,771 A | 5/1997 | Mizukawa et al. | |
| 5,662,680 A | 9/1997 | Desai | |
| 5,695,513 A | 12/1997 | Johnson et al. | |
| 5,697,536 A | 12/1997 | Eggers et al. | |
| 5,810,804 A | 9/1998 | Gough et al. | |
| 5,833,632 A | 11/1998 | Jacobsen et al. | |
| 5,851,212 A | 12/1998 | Zirps et al. | |
| 5,902,251 A | 5/1999 | vanHooydonk | |
| 5,921,956 A * | 7/1999 | Grinberg et al. | 604/95.01 |
| 5,928,239 A | 7/1999 | Mirza | |
| 6,073,051 A | 6/2000 | Sharkey et al. | |
| 6,106,524 A | 8/2000 | Eggers et al. | |
| 6,123,702 A | 9/2000 | Swanson et al. | |
| 6,135,999 A | 10/2000 | Fanton et al. | |
| 6,231,615 B1 | 5/2001 | Preissman | |
| 6,280,441 B1 | 8/2001 | Ryan | |
| 6,409,722 B1 | 6/2002 | Hoey et al. | |
| 6,440,138 B1 | 8/2002 | Reiley et al. | |
| 6,447,506 B1 | 9/2002 | Swanson et al. | |
| 6,464,683 B1 | 10/2002 | Samuelson et al. | |
| 6,478,793 B1 | 11/2002 | Cosman et al. | |
| 6,602,248 B1 | 8/2003 | Sharps et al. | |
| 6,622,731 B2 | 9/2003 | Daniel et al. | |
| 6,863,672 B2 | 3/2005 | Reiley et al. | |
| 6,881,214 B2 | 4/2005 | Cosman et al. | |
| 7,022,133 B2 | 4/2006 | Yee et al. | |
| 7,108,696 B2 | 9/2006 | Daniel et al. | |
| 7,156,843 B2 | 1/2007 | Skarda | |
| 7,186,234 B2 | 3/2007 | Dahla et al. | |
| 7,267,683 B2 | 9/2007 | Sharkey et al. | |
| 7,270,661 B2 | 9/2007 | Dahla et al. | |
| 7,480,533 B2 | 1/2009 | Cosman et al. | |
| 7,503,920 B2 * | 3/2009 | Siegal | 606/79 |
| 7,569,054 B2 | 8/2009 | Michelson | |
| 7,595,634 B2 * | 9/2009 | Flandre et al. | 324/207.2 |
| 7,625,364 B2 | 12/2009 | Corcoran et al. | |
| 7,905,884 B2 * | 3/2011 | Simonton et al. | 606/79 |
| 8,246,627 B2 | 8/2012 | Vanleeuwen et al. | |
| 2002/0133148 A1 | 9/2002 | Daniel et al. | |
| 2003/0014094 A1 | 1/2003 | Hammack et al. | |
| 2003/0130664 A1 | 7/2003 | Boucher et al. | |
| 2004/0087936 A1 | 5/2004 | Stern et al. | |
| 2005/0177210 A1 | 8/2005 | Leung et al. | |
| 2005/0216018 A1 | 9/2005 | Sennett | |
| 2006/0025763 A1 | 2/2006 | Nelson et al. | |
| 2006/0264819 A1 | 11/2006 | Fischer et al. | |
| 2007/0055281 A1 | 3/2007 | Osorio et al. | |
| 2008/0033422 A1 | 2/2008 | Turner et al. | |
| 2008/0058821 A1 | 3/2008 | Maurer et al. | |
| 2008/0183165 A1 | 7/2008 | Buysse et al. | |
| 2008/0208255 A1 | 8/2008 | Siegal | |
| 2008/0228192 A1 | 9/2008 | Beyar et al. | |
| 2008/0249525 A1 | 10/2008 | Lee et al. | |
| 2009/0131948 A1 * | 5/2009 | Liu et al. | 606/93 |
| 2009/0264892 A1 * | 10/2009 | Beyar et al. | 606/94 |
| 2009/0299282 A1 | 12/2009 | Lau et al. | |
| 2010/0082033 A1 | 4/2010 | Germain | |
| 2010/0152724 A1 | 6/2010 | Marion et al. | |
| 2010/0211076 A1 | 8/2010 | Germain et al. | |
| 2011/0160737 A1 | 6/2011 | Steffen et al. | |
| 2011/0251615 A1 | 10/2011 | Truckai et al. | |
| 2011/0295261 A1 | 12/2011 | Germain | |
| 2011/0295262 A1 | 12/2011 | Germain et al. | |
| 2011/0301590 A1 | 12/2011 | Podhajsky et al. | |
| 2012/0130381 A1 | 5/2012 | Germain | |
| 2013/0231654 A1 | 9/2013 | Germain | |
| 2013/0261615 A1 | 10/2013 | Kramer et al. | |
| 2013/0261621 A1 | 10/2013 | Kramer et al. | |

FOREIGN PATENT DOCUMENTS

| | | |
|---|---|---|
| WO | WO 03/101308 | 12/2003 |
| WO | WO 2008/076330 | 6/2008 |
| WO | WO 2008/084479 | 7/2008 |
| WO | WO 2010/039894 | 4/2010 |
| WO | WO 2011/137357 | 11/2011 |
| WO | WO 2011/137377 | 11/2011 |
| WO | WO 2013/147990 | 10/2013 |

* cited by examiner

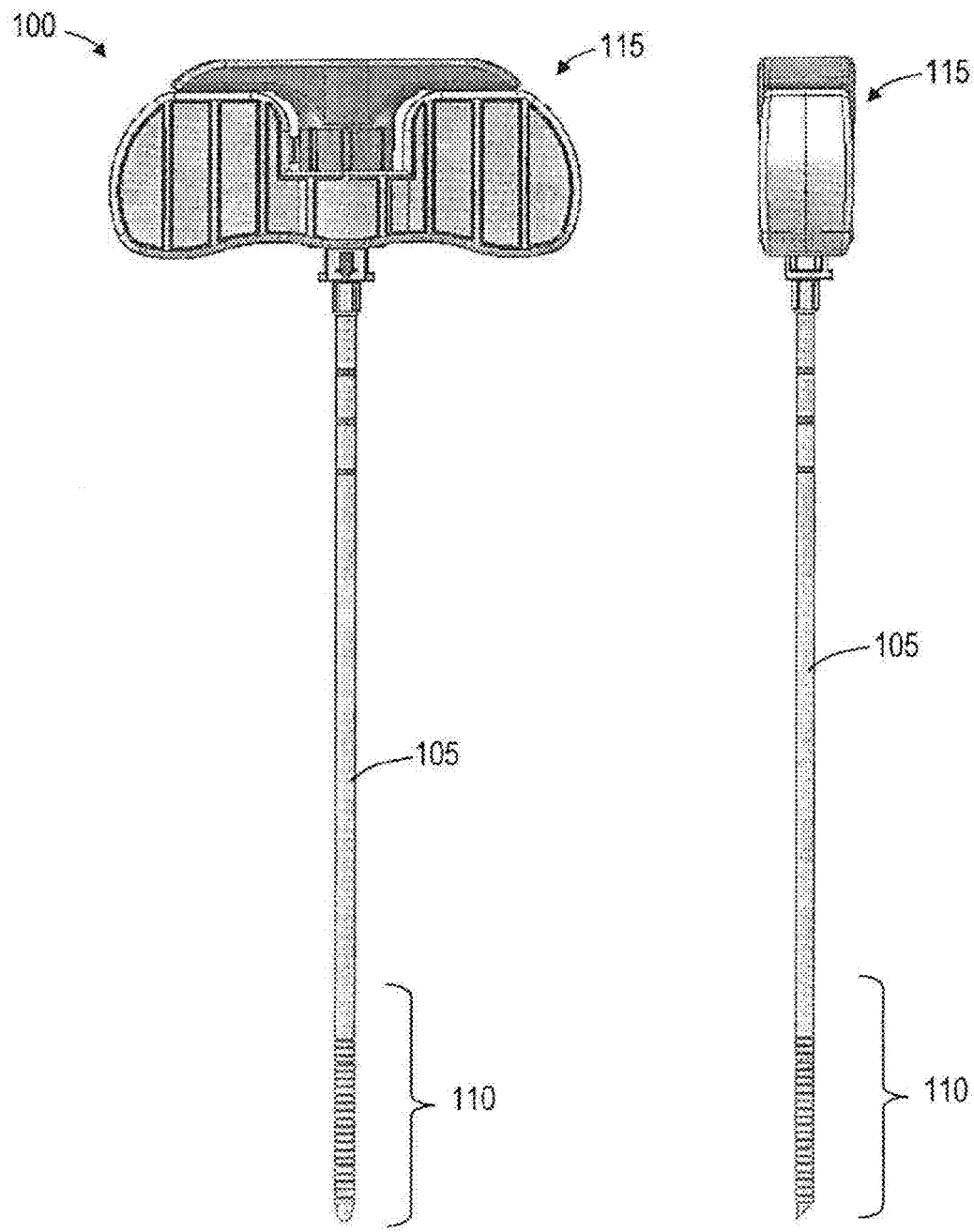

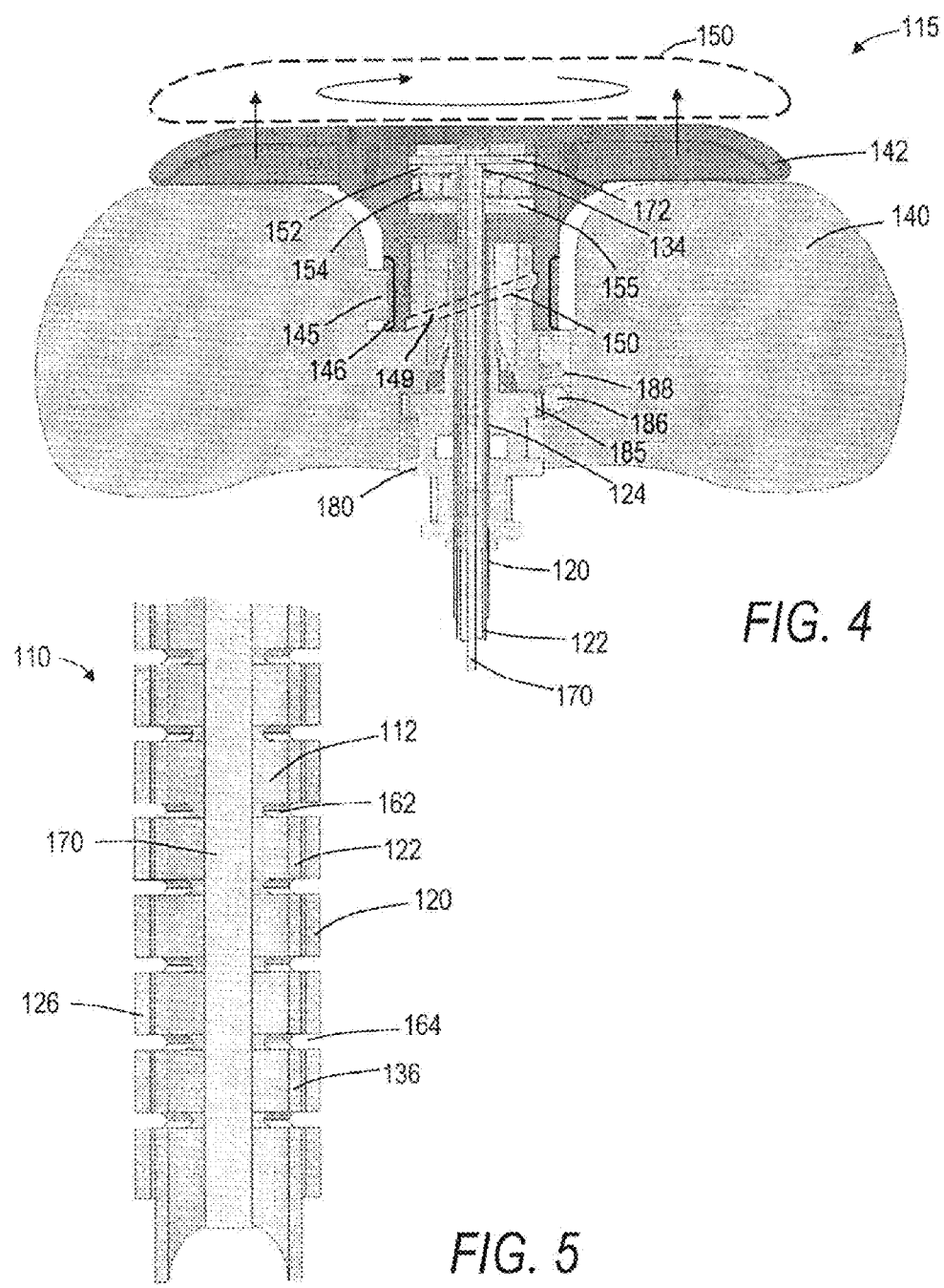

SYSTEMS FOR TREATING A VERTEBRAL BODY

CROSS-REFERENCE TO RELATED APPLICATIONS

This application is a continuation of U.S. patent application Ser. No. 12/578,455, filed on Oct. 13, 2009, which claims the benefit of priority to U.S. Provisional Patent Application No. 61/104,987, filed Oct. 13, 2008, and is a continuation-in-part of U.S. patent application Ser. No. 12/571,174, filed Sep. 30, 2009, now U.S. Pat. No. 8,663,226. The contents of each of which are incorporated herein by reference in its entirety.

FIELD OF THE INVENTION

This invention relates to medical instruments and systems for creating a path or cavity in vertebral bone to receive bone cement to treat a vertebral compression fracture. The features relating to the methods and devices described herein can be applied in any region of bone or hard tissue where the tissue or bone is displaced to define a bore or cavity instead of being extracted from the body such as during a drilling or ablation procedure. In addition, the present invention also discloses methods and devices for ablating or coagulating tissues, including but not limited to ablating tumor tissue in vertebral and/or cortical bone.

SUMMARY OF THE INVENTION

Methods and devices described herein relate to improved creation of a cavity within bone or other hard tissue where the cavity is created by displacement of the tissue. In a first example, a method according to the present disclosure includes treating a vertebral body or other bone structure. In one variation, the method includes providing an elongate tool having a sharp tip configured for penetration into vertebral bone, the tool having an axis extending from a proximal end to a working end thereof, where the working end comprises at least a first sleeve concentrically located within a second sleeve and a third sleeve located concentrically about the second sleeve, where each sleeve comprises a series of slots or notches to limit deflection of the working end to a first curved configuration in a single plane and where the respective series of slots or notches are radially offset in each sleeve; advancing the working end through vertebral bone; causing the working end to move from a linear configuration to a curved configuration by translating the first sleeve relative to the second sleeve in an axial direction; and moving the working end in the curved configuration within the bone to create a cavity therein. Translating of the first sleeve relative to the second sleeve can include moving either sleeve or both sleeves in an axial direction. Additional variations include moving one or both sleeves in a rotational direction to produce relative axial displacement between sleeves.

In an additional variation, the present devices include medical osteotome devices that can for treat a hard tissue (e.g., in a vertebral body) by mechanically displacing the hard tissue and/or applying therapeutic energy to ablate or coagulate tissue. For example, one such variation includes an osteotome type device that is coupled to a power supply and further includes a handle having an actuating portion and a connector for electrically coupling the osteotome device to the power supply; a shaft comprising a first sleeve located concentrically within a second sleeve, the shaft having a distal portion comprising a working end capable of moving between a linear configuration and an articulated configuration where the articulated configuration is limited to a single plane, and where each sleeve comprises a series of slots or notches to limit deflection of the working end to the articulated configuration, where the respective series of slots or notches are radially offset in adjacent sleeves, where a first conductive portion of the shaft is electrically coupleable to a first pole of the power supply; a sharp tip located at a distal tip of the first sleeve of the working end, the sharp tip adapted to penetrate bone within the vertebral body, where the distal tip is coupleable to a second pole of the power supply, such that when activated, current flows between a portion of the distal tip and the shaft; a non-conductive layer electrically isolating the first sleeve from the first conductive portion; and where the shaft and sharp tip have sufficient column strength such that application of an impact force on the handle causes the distal portion of the shaft and the distal tip to mechanically displace the hard tissue. The power supply can be coupled to the outer sleeve (either the second or third sleeve discussed herein.)

Another variations of the method disclosed herein can include the application of energy between electrodes on the device to ablate tissues (e.g., tumor) or to perform other electrosurgical or mapping procedures within the tissue. In one such example for treating a vertebral body, the method can include providing an elongate tool having a sharp tip configured for penetration into vertebral bone, the tool having an axis extending from a proximal end to a working end thereof, where the working end comprises at least a first sleeve concentrically located within a second sleeve, where each sleeve comprises a series of slots or notches to limit deflection of the working end to a first curved configuration in a single plane and where the respective series of slots or notches are radially offset in adjacent sleeves, where a first conductive portion of the first sleeve is electrically coupled to a first pole of a power supply; advancing the working end through vertebral bone; causing the working end to move from a linear configuration to a curved configuration by translating the first sleeve relative to the second sleeve in an axial direction; and applying energy between the first conductive portion and a return electrode electrically coupled to a second pole of the energy supply to ablate or coagulate a region within the vertebral body.

In variations of the method, moving the working end to from the linear configuration to the curved configuration can include moving the working end to move through a plurality of curved configurations.

In an additional variation, causing the working end to move from a linear configuration to the curved configuration comprises actuating a handle mechanism to move the working end from the linear configuration to the curved configuration. The handle mechanism can be moved axially and/or rotationally as described herein.

In one variation, actuating of the handle mechanism causes the working end to move to the first curved configuration without torquing the third sleeve.

In additional variations, the working end of the osteotome or tool is spring biased to assume the linear configuration.

The working end can move from the linear configuration to the curved configuration by applying a driving force or impact to the elongate tool wherein penetration in the cortical bone moves the working end from the linear configuration to the curved configuration. For example, as a hammering or impact force is applied to the working end, the interaction of the sharp tip against bone causes the working end to assume an articulated and/or curved configuration. Where further axial movement of the tool causes compression of the bone and creation of the cavity.

The method can further include the use of one or more cannulae to introduce the tool into the target region. Such a cannula can maintain the tool in a straight or linear configuration until the tool advances out of the cannula or until the cannula is withdrawn from over the tool.

As described herein, upon creation of the cavity, the method can further include the insertion of a filler material or other substance into the cavity. The filler material can be delivered through the tool or through a separate cannula or catheter.

This disclosure also includes variations of devices for creating a cavity within bone or hard tissue. Such variations include devices for treating a vertebral body or other such structure. In one variation a device includes a handle having an actuating portion; a shaft comprising a first sleeve located concentrically within a second sleeve and a third sleeve located concentrically about the second sleeve, the shaft having a distal portion comprising a working end capable of moving between a linear configuration and an articulated configuration where the second articulated configuration is limited to a single plane, and where each sleeve comprises a series of slots or notches to limit deflection of the working end to the articulated configuration, where the respective series of slots or notches are radially offset in each sleeve; and a sharp tip located at a distal tip of the working end, the sharp tip adapted to penetrate vertebral bone within the vertebral body.

In one variation, the devices described herein can include a configuration where the first sleeve is affixed to the second sleeve at the working end such that proximal movement of the first sleeve causes the working end to assume the articulated configuration. The sleeves can be affixed at any portion along their length via a mechanical fixation means (e.g., a pin or other fixation means), an adhesive, or one or more weld points. In some variations, fixation of the sleeves occurs at the working end so that movement of the inner or first sleeve causes the working end to assume the curved configuration. In some cases, the third sleeve can be affixed outside of the working end so long as when the first and second sleeves articulate, the third sleeve still articulates.

Devices described herein can optionally include a force-limiting assembly coupled between the actuating portion and the first sleeve such that upon reaching a threshold force, the actuating portion disengages the first sleeve. In one variation, the force-limiting mechanism is adapted to limit force applied to bone when moving the working end from the first configuration toward the second configuration.

In additional variations, devices for creating cavities in bone or hard tissue can include one or more spring elements that extending through the first sleeve, where the spring element is affixed to the shaft (within or about either the first, second, or third sleeve). Such spring elements cause the working end to assume a linear configuration in a relaxed state.

In additional variations, a device can include an outer or third sleeve where the slots or notches (that allow deflection) are located on an exterior surface of the third sleeve. The exterior surface is typically the surface that faces outward from a direction of the curved configuration. This configuration allows for an interior surface (the surface located on the interior of the curved portion) to be smooth. As a result, if the device is withdrawn through tissue or a cannula or other introducer, the smooth surface on the interior of the curve minimizes the chance that the device becomes caught on the opening of the cannula or any other structure.

Variations of the device can include one or more lumens that extend through the shaft and working end. These lumens can exit at a distal tip of the device or through a side opening in a wall of the device. The lumen can include a surface comprising a lubricious polymeric material. For example, the material can comprise any bio-compatible material having low frictional properties (e.g., TEFLON®, a polytetrafluoroethylene (PTFE), FEP (Fluorinated ethylenepropylene), polyethylene, polyamide, ECTFE (Ethylenechlorotrifluoroethylene), ETFE, PVDF, polyvinyl chloride and silicone).

As described herein, the devices can include any number of configurations to prevent rotation between adjacent sleeves but allow axial movement between the sleeves. For example, the sleeves can be mechanically coupled via a pin/slot or key/keyway configuration. In an additional variation, the sleeves can be non-circular to prevent rotation.

In an additional variation, the disclosure includes various kits comprising the device described herein as well as a filler material (e.g., a bone cement or other bone filler material).

Variations of the access device and procedures described above include combinations of features of the various embodiments or combination of the embodiments themselves wherever possible.

BRIEF DESCRIPTION OF DRAWINGS

FIG. 1 is a plan view of an osteotome of the invention.
FIG. 2 is a side view of the osteotome of FIG. 1.
FIG. 4 is an enlarged sectional view of the handle of the osteotome of FIG. 1.
FIG. 5 is an enlarged sectional view of the working end of the osteotome of FIG. 1.

DETAILED DESCRIPTION

Figure 3:
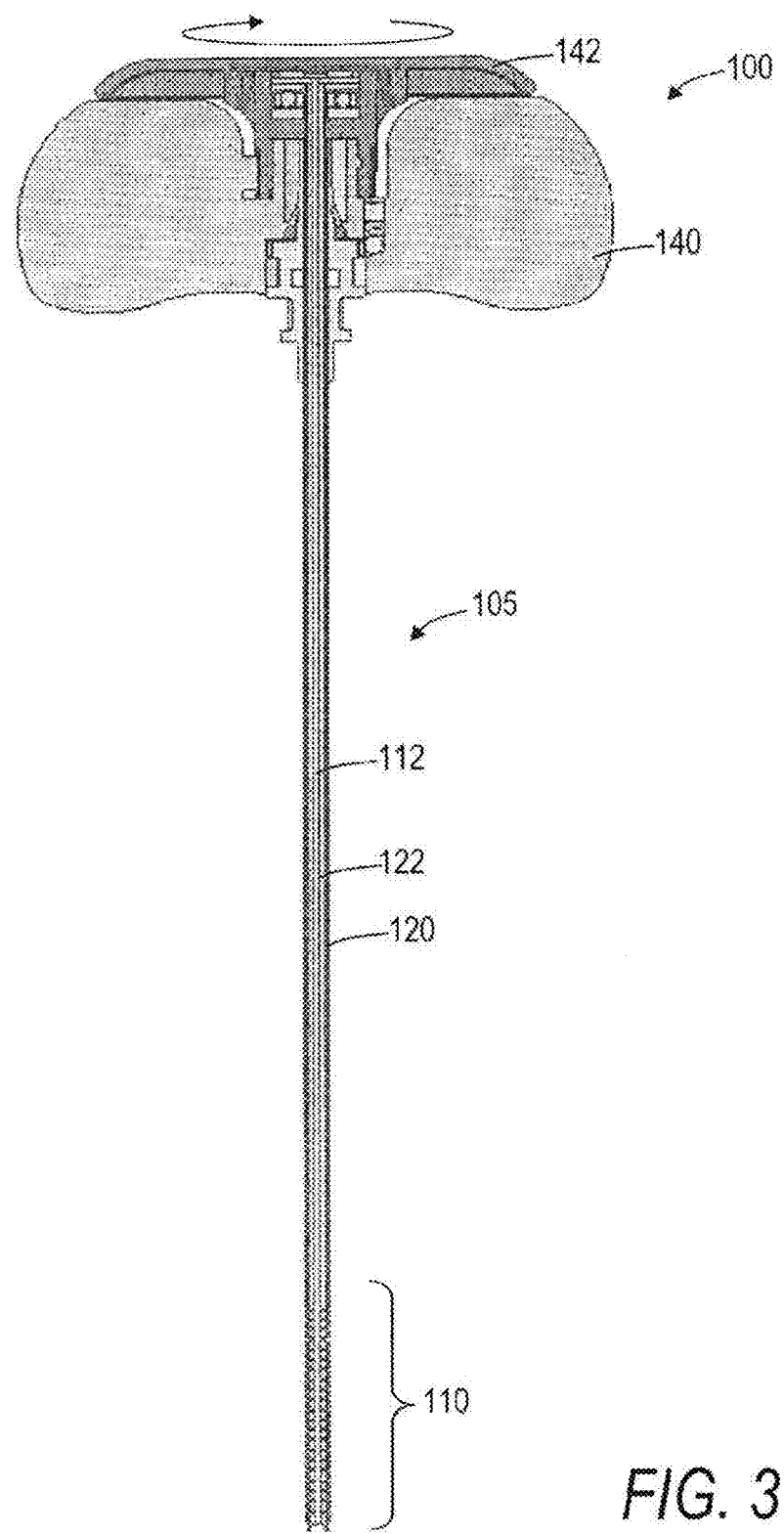
FIG. 3 is a cross sectional view of the osteotome of FIG. 1.

Referring to FIGS. 1-5, an apparatus or osteotome 100 is shown that is configured for accessing the interior of a vertebral body and for creating a pathway in vertebral cancellous bone to receive bone cement. In one embodiment, the apparatus is configured with an extension portion or member 105 for introducing through a pedicle and wherein a working end 110 of the extension member can be progressively actuated to curve a selected degree and/or rotated to create a curved pathway and cavity in the direction of the midline of the vertebral body. The apparatus can be withdrawn and bone fill material can be introduced through a bone cement injection cannula. Alternatively, the apparatus 100 itself can be used as a cement injector with the subsequent injection of cement through a lumen 112 of the apparatus.

In one embodiment, the apparatus 100 comprises a handle 115 that is coupled to a proximal end of the extension member 105. The extension member 105 comprises an assembly of first (outer) sleeve 120 and a second (inner) sleeve 122, with the first sleeve 120 having a proximal end 124 and distal end 126. The second sleeve 122 has a proximal end 134 and distal end 136. The extension member 105 is coupled to the handle 115, as will be described below, to allow a physician to drive the extension member 105 into bone while contemporaneously actuating the working end 110 into an actuated or curved configuration (see FIG. 6). The handle 115 can be fabricated of a polymer, metal or any other material suitable to withstand hammering or impact forces used to drive the assembly into bone (e.g., via use of a hammer or similar device on the handle 115). The inner and outer sleeves are fabricated of a suitable metal alloy, such as stainless steel or NiTi. The wall thicknesses of the inner and outer sleeves can range from about 0.005" to 0.010" with the outer diameter the outer sleeve ranging from about 2.5 mm to 5.0 mm.

Referring to FIGS. 1, 3 and 4, the handle 115 comprises both a first grip portion 140 and a second actuator portion indicated at 142. The grip portion 140 is coupled to the first sleeve 120 as will be described below. The actuator portion 142 is operatively coupled to the second sleeve 122 as will be described below. The actuator portion 142 is rotatable relative to the grip portion 140 and one or more plastic flex tabs 145 of the grip portion 140 are configured to engage notches 146 in the rotatable actuator portion 142 to provide tactile indication and temporary locking of the handle portions 140 and 142 in a certain degree of rotation. The flex tabs 145 thus engage and disengage with the notches 146 to permit ratcheting (rotation and locking) of the handle portions and the respective sleeve coupled thereto.

The notches or slots in any of the sleeves can comprise a uniform width along the length of the working end or can comprise a varying width. Alternatively, the width can be selected in certain areas to effectuate a particular curved profile. In other variation, the width can increase or decrease along the working end to create a curve having a varying radius. Clearly, it is understood that any number of variations are within the scope of this disclosure.

FIG. 4 is a sectional view of the handle showing a mechanism for actuating the second inner sleeve 122 relative to the first outer sleeve 120. The actuator portion 142 of the handle 115 is configured with a fast-lead helical groove indicated at 150 that cooperates with a protruding thread 149 of the grip portion 140 of the handle. Thus, it can be understood that rotation of the actuation portion 142 will move this portion to the position indicated at 150 (phantom view). In one embodiment, when the actuator portion 142 is rotated a selected amount from about 45° to 720°, or from about 90° to 360°, the inner sleeve 122 is lifted proximally relative to the grip portion 140 and outer sleeve 120 to actuate the working end 110. As can be seen in FIG. 4 the actuator portion 142 engages flange 152 that is welded to the proximal end 132 of inner sleeve 122. The flange 152 is lifted by means of a ball bearing assembly 154 disposed between the flange 152 and metal bearing surface 155 inserted into the grip portion 140 of the handle. Thus, the rotation of actuator 142 can lift the inner sleeve 122 without creating torque on the inner sleeve.

Figure 6A:
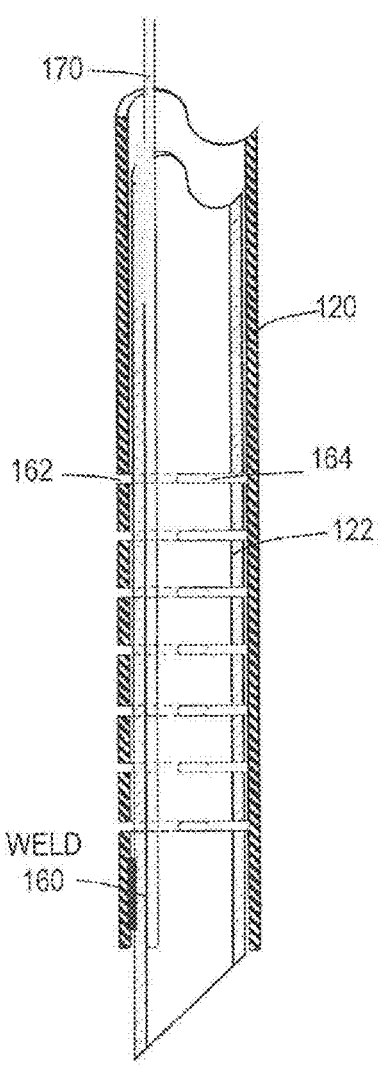
FIG. 6A is a sectional view of the working end of FIG. 5 in a linear configuration.
Figure 6B:
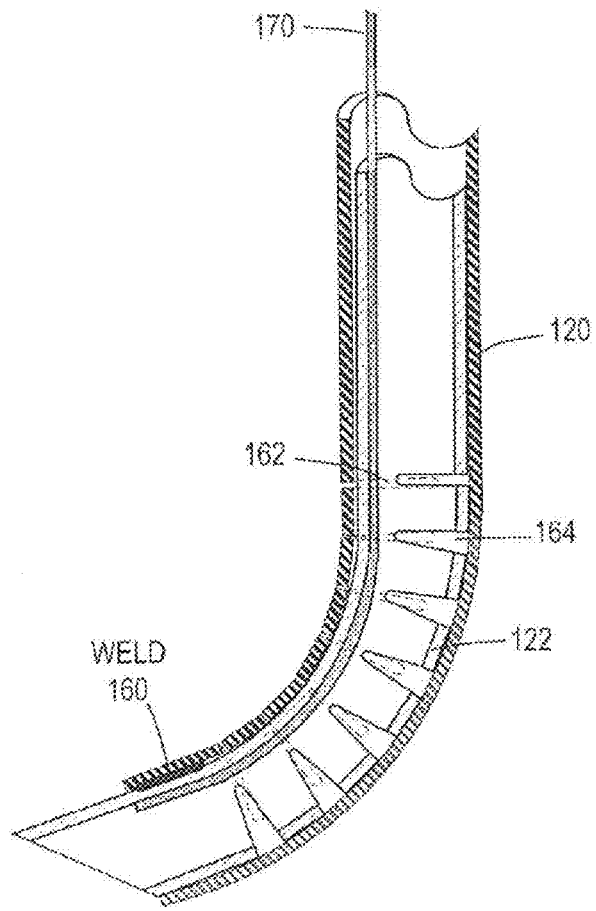
FIG. 6B is a sectional view of the working end of FIG. 5 in a curved configuration.

Now turning to FIGS. 5, 6A and 6B, it can be seen that the working end 110 of the extension member 105 is articulated by cooperating slotted portions of the distal portions of outer sleeve 120 and inner sleeve 122 that are both thus capable of bending in a substantially tight radius. The outer sleeve 120 has a plurality of slots or notches 162 therein that can be any slots that are perpendicular or angled relative to the axis of the sleeve. The inner sleeve 122 has a plurality of slots or notches indicated at 164 that can be on an opposite side of the assembly relative to the slots 162 in the outer sleeve 120. The outer and inner sleeves are welded together at the distal region indicated at weld 160. It thus can be understood that when inner sleeve 122 is translated in the proximal direction, the outer sleeve will be flexed as depicted in FIG. 6B. It can be understood that by rotating the actuator handle portion 142 a selected amount, the working end can be articulated to a selected degree.

FIGS. 4, 5, 6A and 6B further illustrate another element of the apparatus that comprises a flexible flat wire member 170 with a proximal end 171 and flange 172 that is engages the proximal side of flange 152 of the inner sleeve 122. At least the distal portion 174 of the flat wire member 170 is welded to the inner sleeve at weld 175. This flat wire member thus provides a safety feature to retain the working end in the event that the inner sleeve fails at one of the slots 164.

Another safety feature of the apparatus comprises a torque limiter and release system that allows the entire handle assembly 115 to freely rotate—for example if the working end 110 is articulated, as in FIG. 6B, when the physician rotates the handle and when the working end is engaged in strong cancellous bone. Referring to FIG. 4, the grip portion 142 of the handle 115 engages a collar 180 that is fixed to a proximal end 124 of the outer sleeve 120. The collar 180 further comprises notches 185 that are radially spaced about the collar and are engaged by a ball member 186 that is pushed by a spring 188 into notches 185. At a selected force, for example a torque ranging from greater than about 0.5 inch*lbs but less that about 7.5 inch*lbs, 5.0 inch*lbs or 2.5 inch*lbs, the rotation of the handle 115 overcomes the predetermined limit. When the torque limiter assembly is in its locked position, the ball bearing 186 is forced into one of the notches 185 in the collar 180. When too much torque is provided to the handle and outer sleeve, the ball bearing 186 disengages the notch 185 allowing the collar 180 to turn, and then reengages at the next notch, releasing anywhere from 0.5 inch*lbs to 7.5 inch*lbs of torque.

Referring to FIGS. 6A and 6B, it can be understood that the inner sleeve 122 is weakened on one side at its distal portion so as to permit the inner sleeve 122 to bend in either direction but is limited by the location of the notches in the outer sleeve 120. The curvature of any articulated configuration is controlled by the spacing of the notches as well as the distance between each notch peak. The inner sleeve 122 also has a beveled tip for entry through the cortical bone of a vertebral body. Either the inner sleeve or outer sleeve can form the distal tip.

Figure 7A:
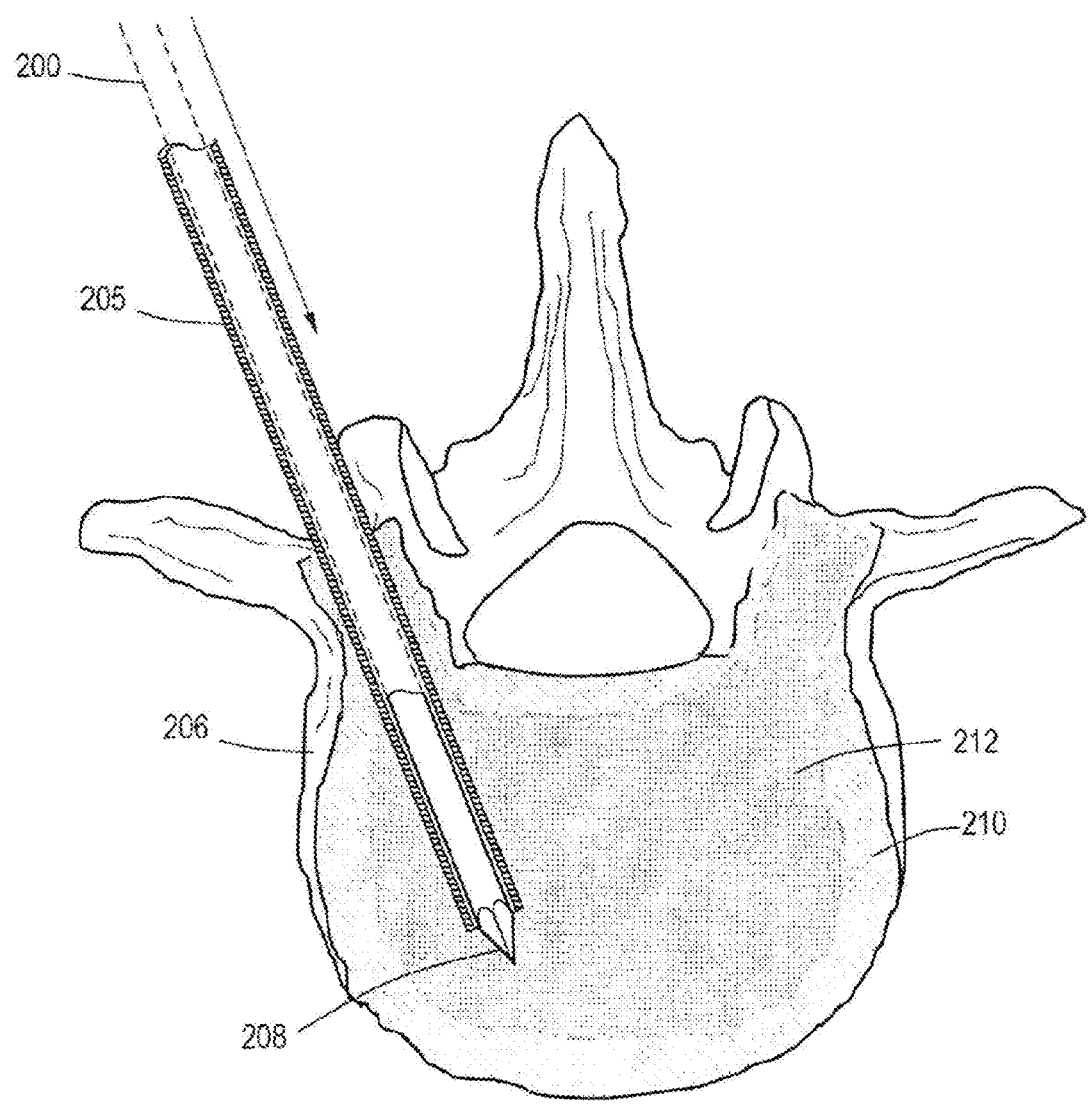
FIGS. 7A-7C are schematic sectional views of a method of use of the osteotome of FIG. 1.
Figure 7B:
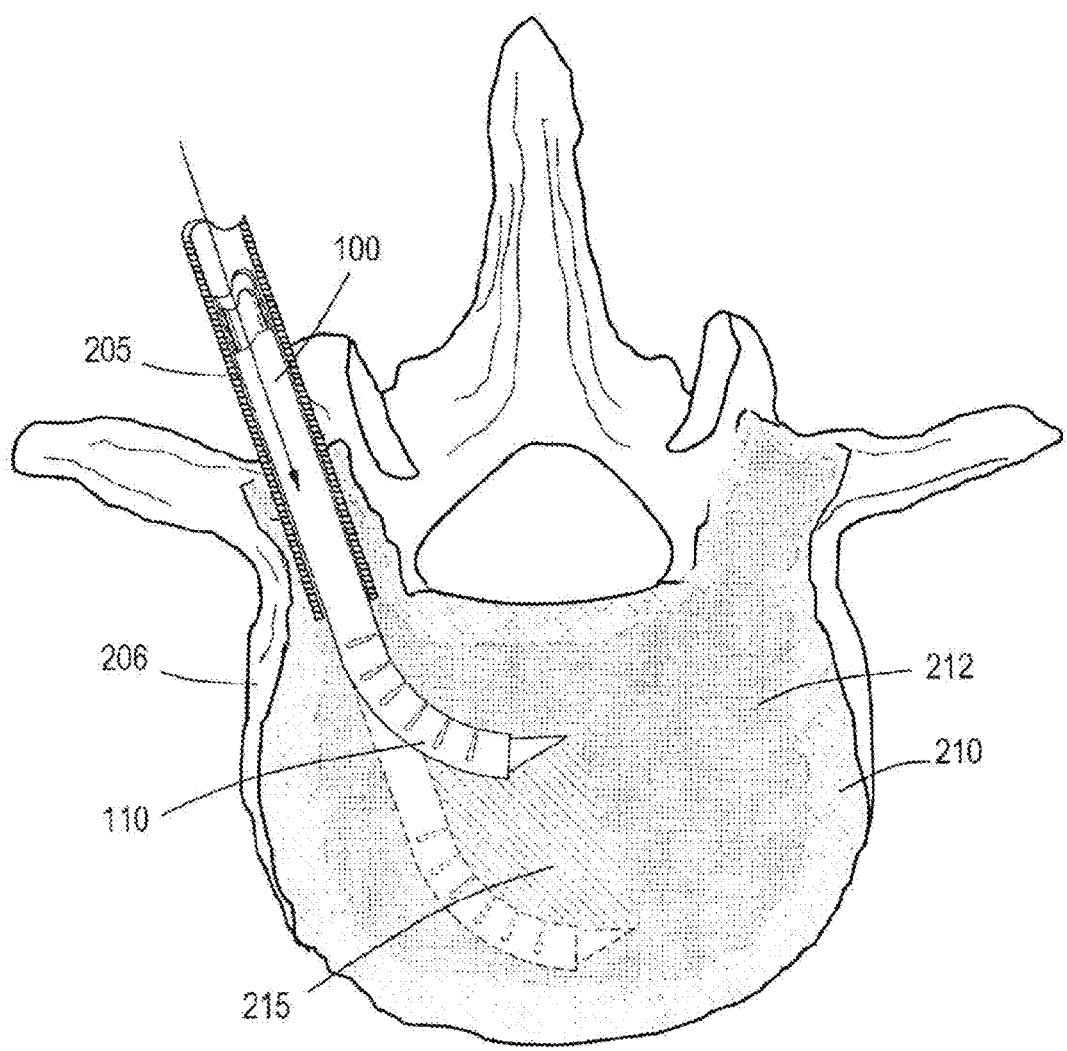
Figure 7C:
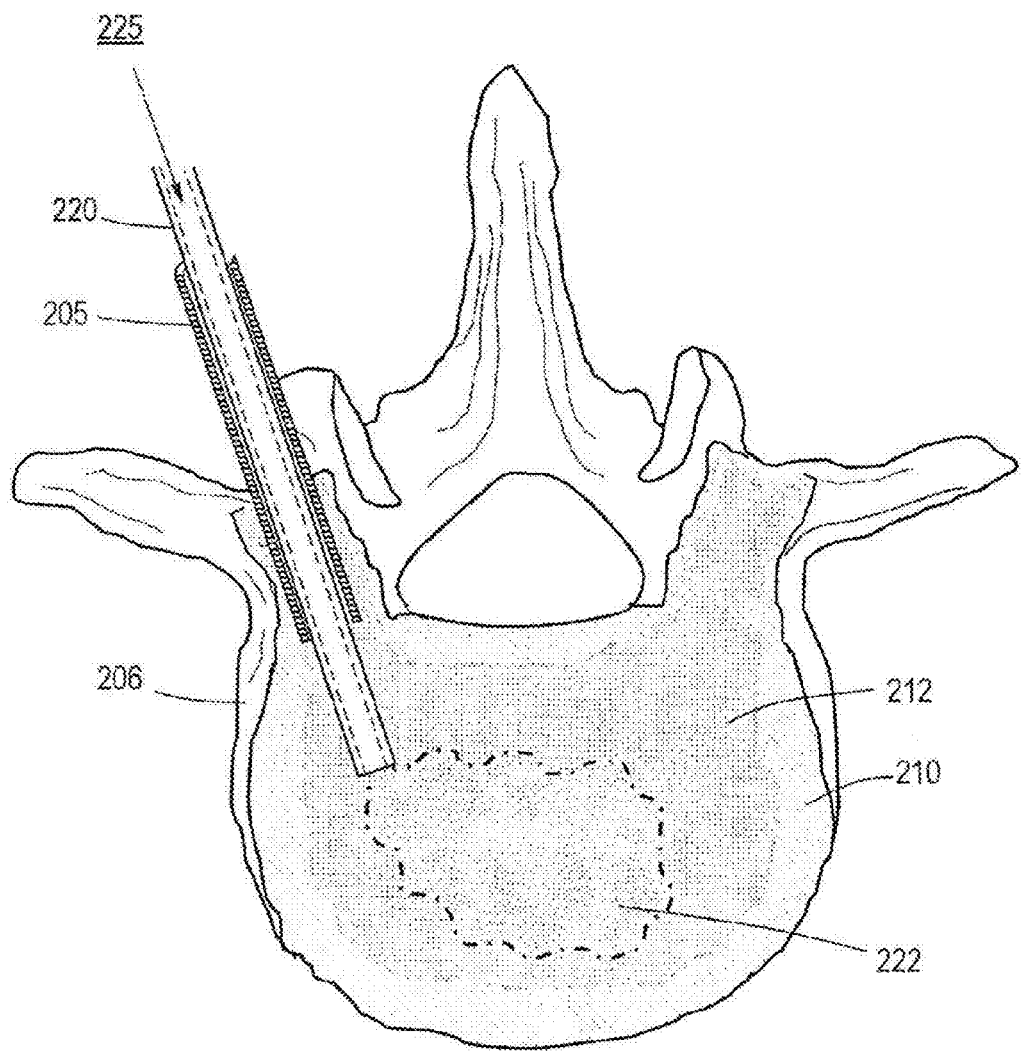

Referring to FIGS. 7A-7C, in one variation of use of the device, a physician taps or otherwise drives a stylet 200 and introducer sleeve 205 into a vertebral body 206 typically until the stylet tip 208 is within the anterior ⅓ of the vertebral body toward cortical bone 210 (FIG. 7A). Thereafter, the stylet 200 is removed and the sleeve 205 is moved proximally (FIG. 7B). As can be seen in FIG. 7B, the tool or osteotome 100 is inserted through the introducer sleeve 205 and articulated in a series of steps as described above. The working end 110 can be articulated intermittently while applying driving forces and optionally rotational forces to the handle 115 to advance the working end through the cancellous bone 212 to create path or cavity 215. The tool is then tapped to further drive the working end 110 to, toward or past the midline of the vertebra. The physician can alternatively articulate the working end 110, and drive and rotate the working end further until imaging shows that the working end 100 has created a cavity 215 of an optimal configuration. Thereafter, as depicted in FIG. 7C, the physician reverses the sequence and progressively straightens the working end 110 as the extension member is withdrawn from the vertebral body 206. Thereafter, the physician can insert a bone cement injector 220 into the path or cavity 215 created by osteotome 100. FIG. 7C illustrates a bone cement 222, for example a PMMA cement, being injected from a bone cement source 225.

In another embodiment (not shown), the apparatus 100 can have a handle 115 with a Luer fitting for coupling a bone cement syringe and the bone cement can be injected through the lumen 112 of the apparatus. In such an embodiment FIG. 9, the lumen can have a lubricious surface layer or polymeric lining 250 to insure least resistance to bone cement as it flows through the lumen. In one embodiment, the surface or lining 250 can be a fluorinated polymer such as TEFLON® or polytetrafluroethylene (PTFE). Other suitable fluoropolymer resins can be used such as FEP and PFA. Other materials also can be used such as FEP (Fluorinated ethylenepropylene), ECTFE (Ethylenechlorotrifluoro-ethylene), ETFE, Polyethylene, Polyamide, PVDF, Polyvinyl chloride and silicone. The scope of the invention can include providing a polymeric material having a static coefficient of friction of less than 0.5, less than 0.2 or less than 0.1.

Figure 9:
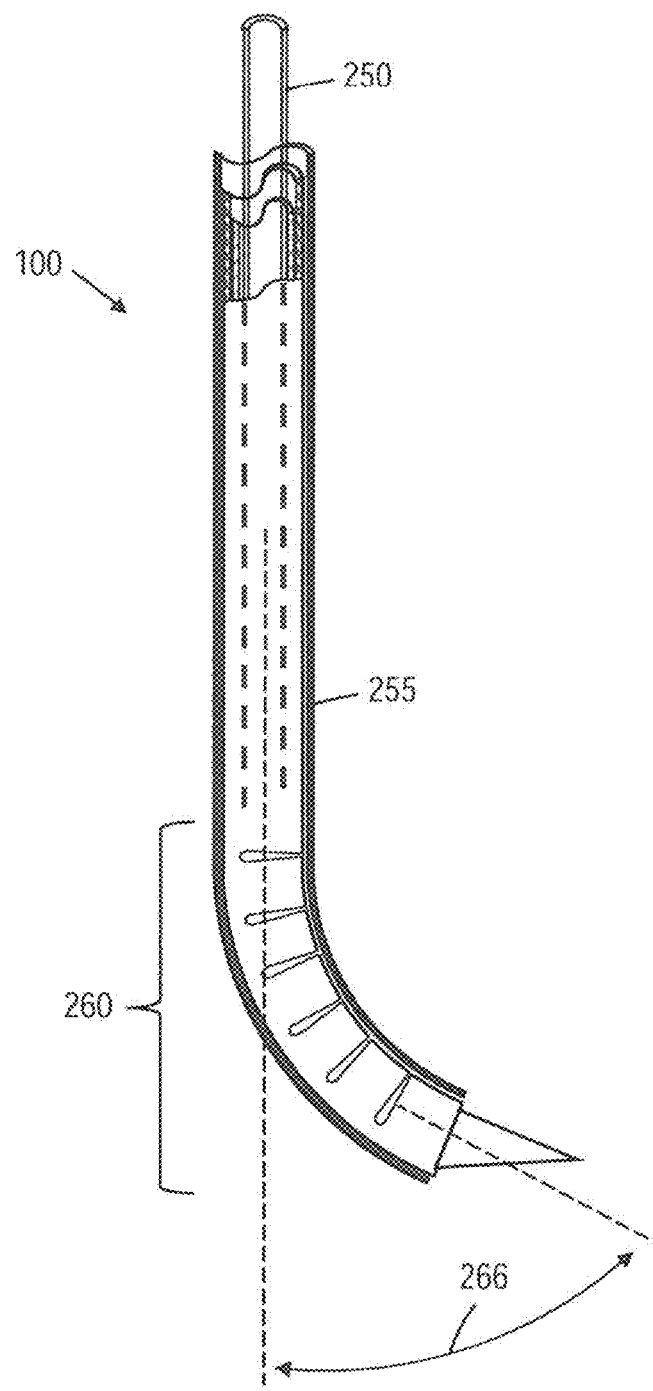
FIG. 9 is another embodiment of an osteotome working end.

FIG. 9 also shows the extension member or shaft 105 can be configured with an exterior flexible sleeve indicated at 255. The flexible sleeve can be any commonly known biocompatible material, for example, the sleeve can comprise any of the materials described in the preceding paragraph.

As also can be seen in FIG. 9, in one variation of the device 100, the working end 110 can be configured to deflect over a length indicated at 260 in a substantially smooth curve. The degree of articulation of the working end 100 can be at least 45°, 90°, 135° or at least 180° as indicated at 265 (FIG. 9). In additional variations, the slots of the outer 120 and inner sleeves 120 can be varied to produce a device having a radius of curvature that varies among the length 260 of the device 100.

In another embodiment of the invention, the inner sleeve can be spring loaded relative the outer sleeve, in such a way as to allow the working end to straighten under a selected level of force when pulled in a linear direction. This feature allows the physician to withdraw the assembly from the vertebral body partly or completely without further rotation the actuating portion 142 of handle 115. In some variations, the force-limiter can be provided to allow less than about 10 inch*lbs of force to be applied to bone.

Figure 8:
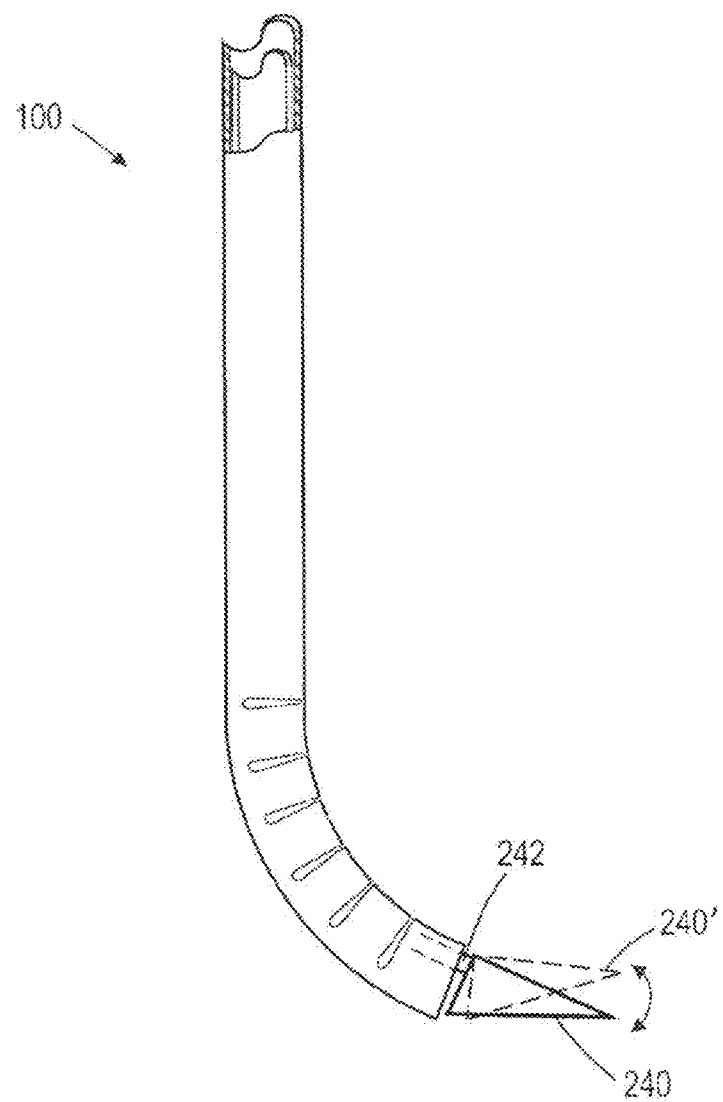
FIG. 8 is another embodiment of an osteotome working end.

In another embodiment shown in FIG. 8, the working end 110 is configured with a tip 240 that deflects to the position indicated at 240' when driven into bone. The tip 240 is coupled to the sleeve assembly by resilient member 242, for example a flexible metal such as stainless steel or NiTi. It has been found that the flexing of the tip 240 causes its distal surface area to engage cancellous bone which can assist in deflecting the working end 110 as it is hammered into bone.

In another embodiment of the invention (not shown), the actuator handle can include a secondary (or optional) mechanism for actuating the working end. The mechanism would include a hammer-able member with a ratchet such that each tap of the hammer would advance assembly and progressively actuate the working end into a curved configuration. A ratchet mechanism as known in the art would maintain the assembly in each of a plurality of articulated configurations. A release would be provided to allow for release of the ratchet to provide for straightening the extension member 105 for withdrawal from the vertebral body.

Figure 10:
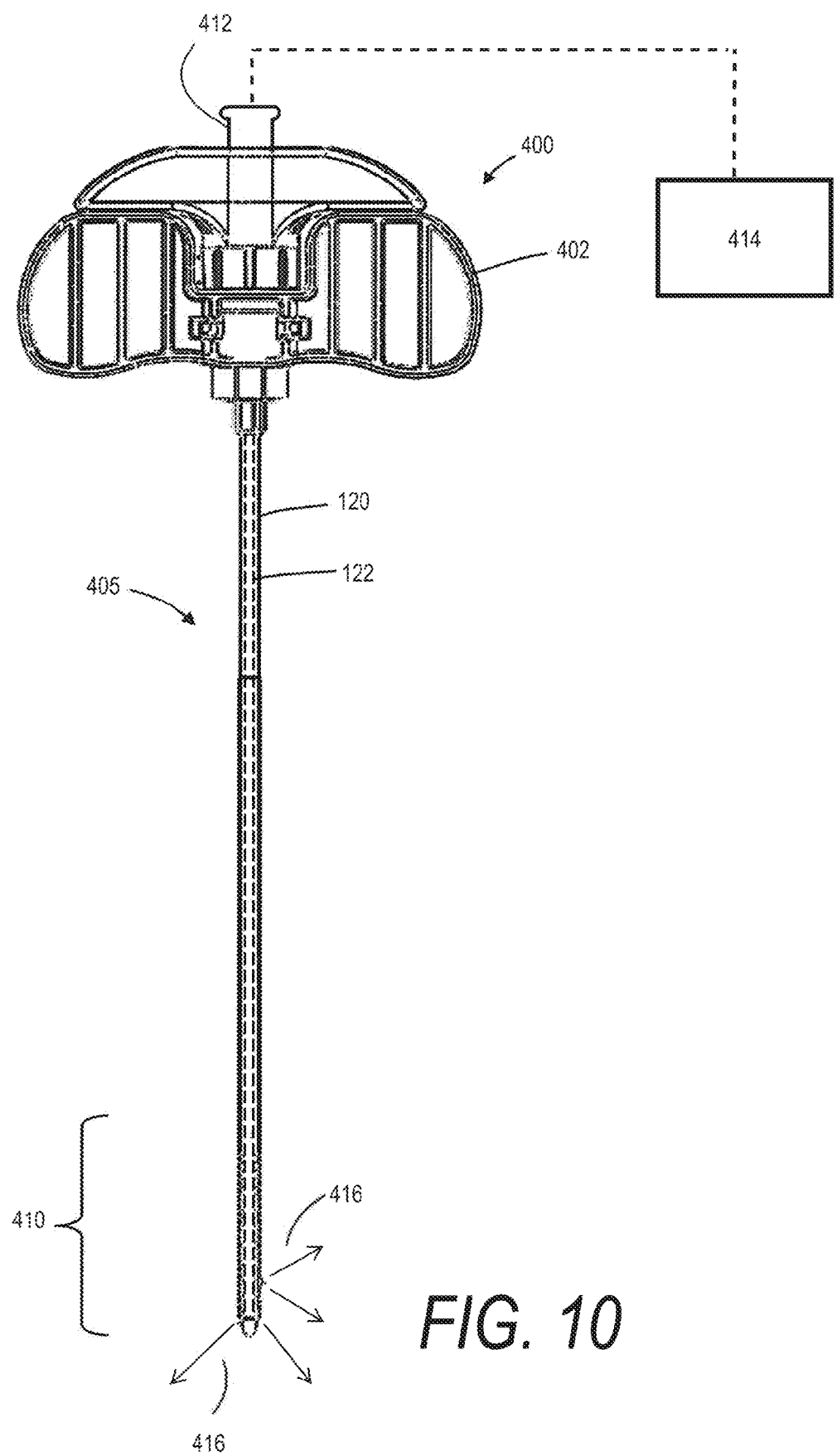
FIG. 10 is another variation of an osteotome with an outer sleeve.
Figure 11:
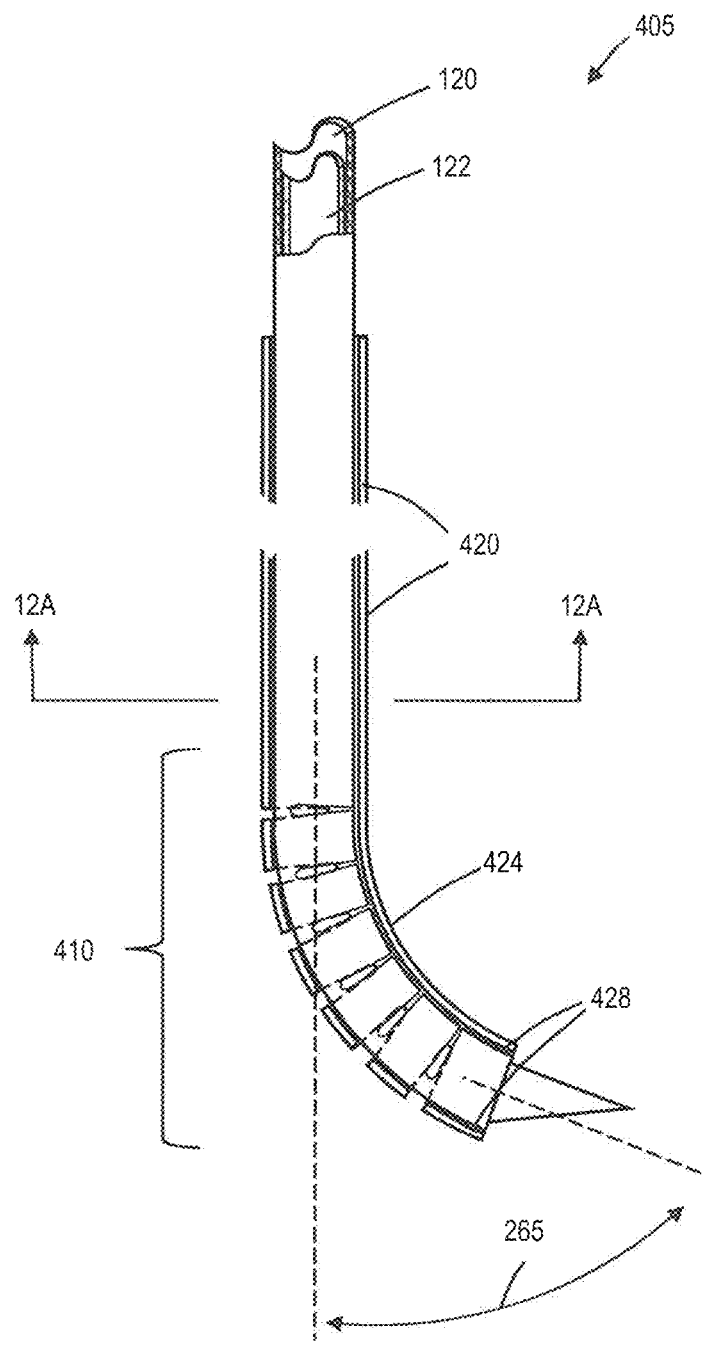
FIG. 11 is a cut-away view of the working end of the osteotome of FIG. 10.

FIGS. 10 and 11 illustrate another variation of a bone treatment device 400 with a handle 402 and extension member 405 extending to working end 410 having a similar construction to that FIGS. 1 to 6B. The device 400 operates as described previously with notched first (outer) sleeve 120 and cooperating notched second (inner) sleeve 122. However, the variation shown in FIGS. 10 and 11 also includes a third concentric notched sleeve 420, exterior to the first 120 and second 122 sleeves. The notches or slots in sleeve 420 at the working end 410 permit deflection of the sleeve as indicated at 265 in FIG. 11.

FIG. 10 also illustrates the treatment device 400 as including a luer fitting 412 that allows the device 402 to be coupled to a source of a filler material (e.g., a bone filler or bone cement material). The luer can be removable from the handle 402 to allow application of an impact force on the handle as described above. Moreover, the luer fitting 402 can be located on the actuating portion of the handle, the stationary part of the handle or even along the sleeve. In any case, variations of the device 400 permit coupling the filler material with a lumen extending through the sleeves (or between adjacent sleeves) to deposit filler material at the working end 410. As shown by arrows 416, filler material can be deposited through a distal end of the sleeves (where the sharp tip is solid) or can be deposited through openings in a side-wall of the sleeves. Clearly, variations of this configuration are within the scope of those familiar in the field.

In some variations, the third notched sleeve 420 is configured with its smooth (non-notched) surface 424 disposed to face inwardly on the articulated working end (FIG. 11) such that a solid surface forms the interior of the curved portion of the working end 410. The smooth surface 424 allows withdrawal of the device 110 into a cannula or introducer 205 without creating a risk that the slots or notches become caught on a cannula 205 (see e.g., FIG. 7B).

As shown in FIGS. 10-11, the third (outermost) sleeve 420 can extend from an intermediate location on the extension member 405 to a distal end of the working end 410. However, variations of the device include the third sleeve 420 extending to the handle 402. However, the third sleeve 420 is typically not coupled to the handle 402 so that any rotational force or torque generated by the handle 402 is not directly transmitted to the third sleeve 420.

In one variation, the third sleeve 420 is coupled to the second sleeve 120 at only one axial location. In the illustrated example shown in FIG. 11, the third sleeve 420 is affixed to second sleeve 420 by welds 428 at the distal end of the working end 410. However, the welds or other attachment means (e.g., a pin, key/keyway, protrusion, etc.) can be located on a medial part of the sleeve 420. The sleeve 420 can be fabricated of any bio-compatible material. For example, in one variation, the third sleeve is fabricated form a 3.00 mm diameter stainless steel material with a wall thickness of 0.007". The first, second and third sleeves are sized to have dimensions to allow a sliding fit between the sleeves.

Figure 12A:
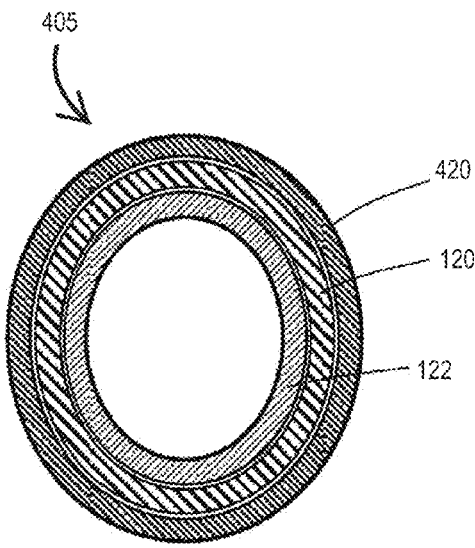
FIG. 12A is sectional view of another embodiment of working end, taken along line 12A-12A of FIG. 11.
Figure 12C:
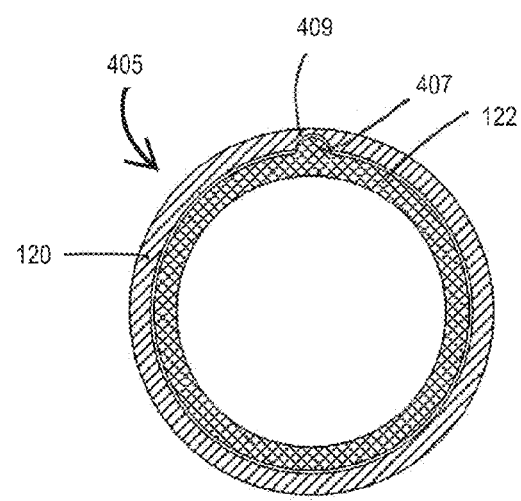
FIGS. 12B and 12C illustrate additional variations of preventing rotation between adjacent sleeves.
Figure 12B:
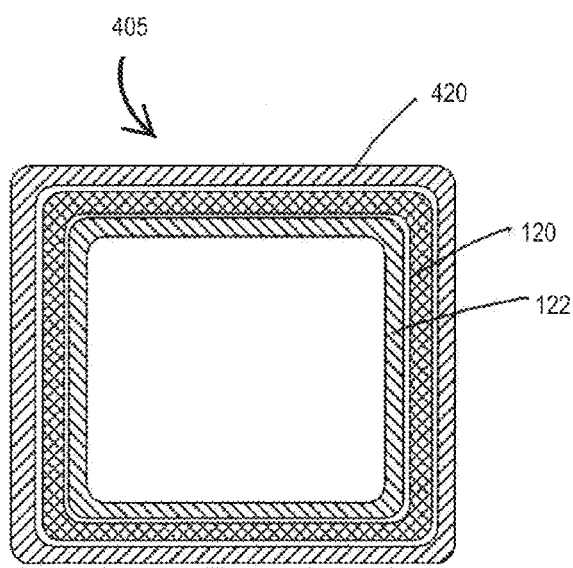

FIG. 12A is a sectional view of extension member 405 of another variation, similar to that shown in FIGS. 10-11. However, the variation depicted by FIG. 12A comprises non-round configurations of concentric slidable sleeves (double or triple sleeve devices). This configuration limits or prevents rotation between the sleeves and allows the physician to apply greater forces to the bone to create a cavity. While FIG. 12A illustrates an oval configuration, any non-round shape is within the scope of this disclosure. For example, the cross-sectional shape can comprise a square, polygonal, or other radially keyed configuration as shown in FIGS. 12B and 12C. As shown in FIG. 12C the sleeves can include a key 407 and a receiving keyway 409 to prevent rotation but allow relative or axial sliding of the sleeves. The key can comprise any protrusion or member that slides within a receiving keyway. Furthermore, the key can comprise a pin or any raised protrusion on an exterior or interior of a respective sleeve. In this illustration, only the first 122 and second 120 sleeves are illustrated. However, any of the sleeves can be configured with the key/keyway. Preventing rotation between sleeves improves the ability to apply force to bone at the articulated working end.

Figure 13:
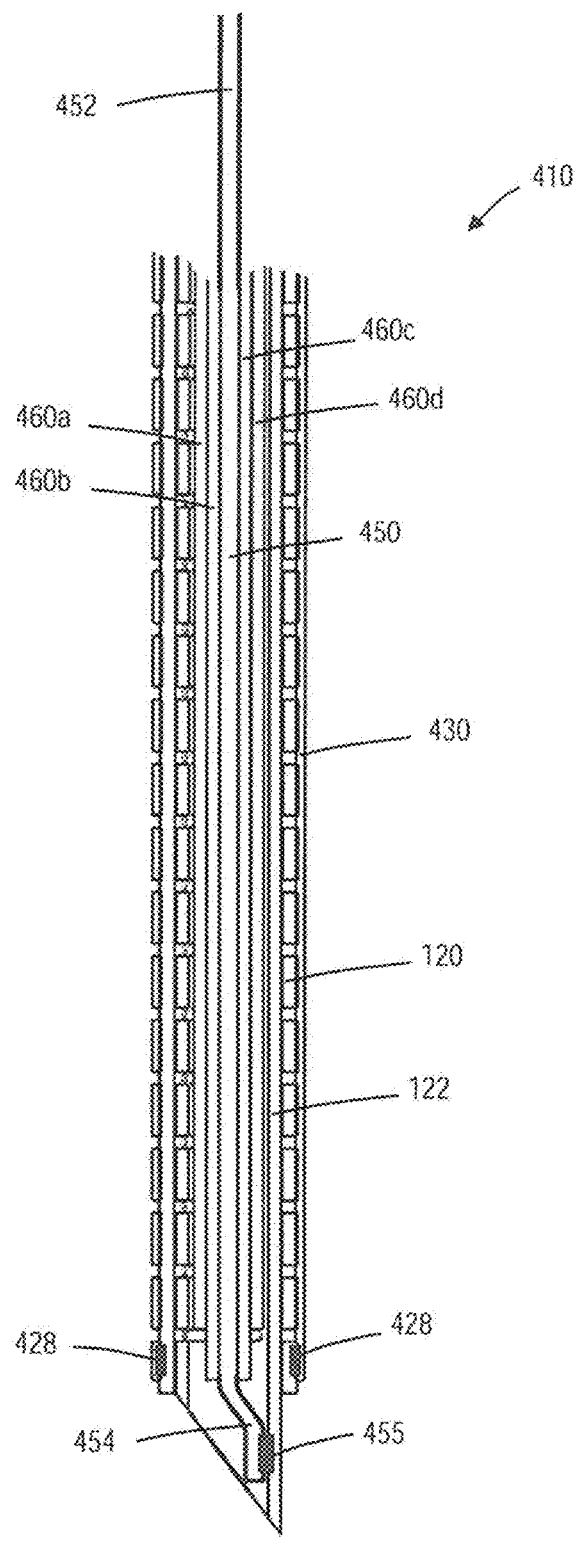
FIG. 13 is sectional view of another working end embodiment similar to that of FIG. 11.
Figure 14:
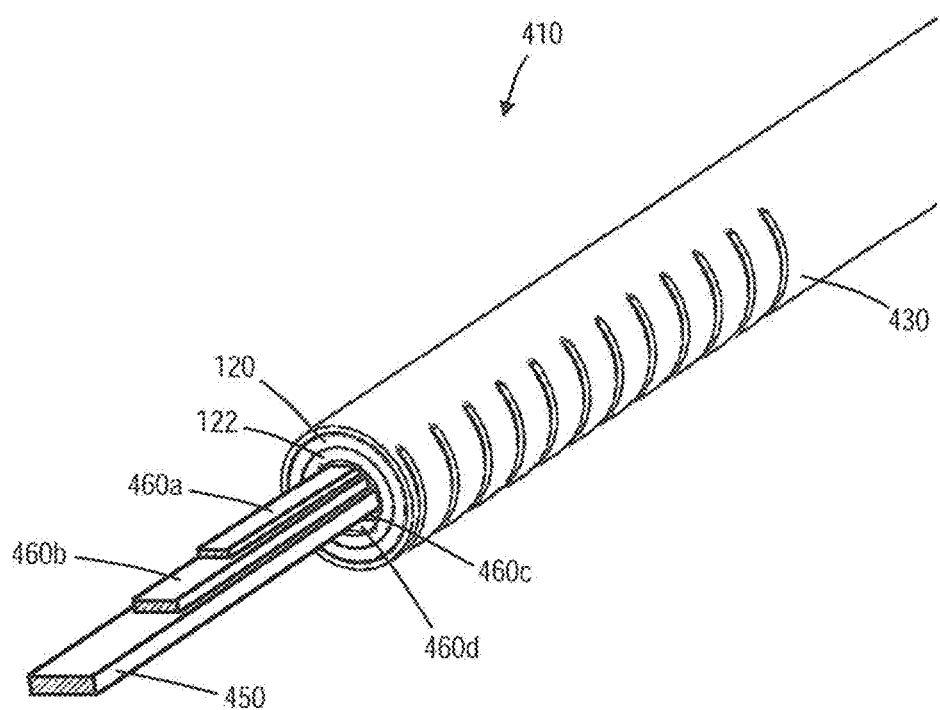
FIG. 14 is a cut-away perspective view of the working end of FIG. 13.

FIGS. 13-14 illustrate another variation of a working end 410 of an osteotome device. In this variation, the working end 410 includes one or more flat spring elements 450, 460a, 460b, 460c, 460d, that prevent relative rotation of the sleeves of the assembly thus allowing greater rotational forces to be applied to cancellous bone from an articulated working end. The spring elements further urge the working end assembly into a linear configuration. To articulate the sleeves, a rotational force is applied to the handle as described above, once this rotational force is removed, the spring elements urge the working end into a linear configuration. As shown in FIG. 13, one or more of the spring elements can extend through the sleeves for affixing to a handle to prevent rotation. Furthermore, the distal end 454 of flat spring element 450 is fixed to sleeve assembly by weld 455. Thus, the sprint element is fixed at each end to prevent its rotation. Alternate variations include one or more spring elements being affixed to the inner sleeve assembly at a medial section of the sleeve.

As shown in FIGS. 13-14, variations of the osteotome can include any number of spring elements 460a-460d. These additional spring elements 460a-460d can be welded at either a proximal or distal end thereof to an adjacent element or a sleeve to allow the element to function as a leaf spring.

Figure 15:
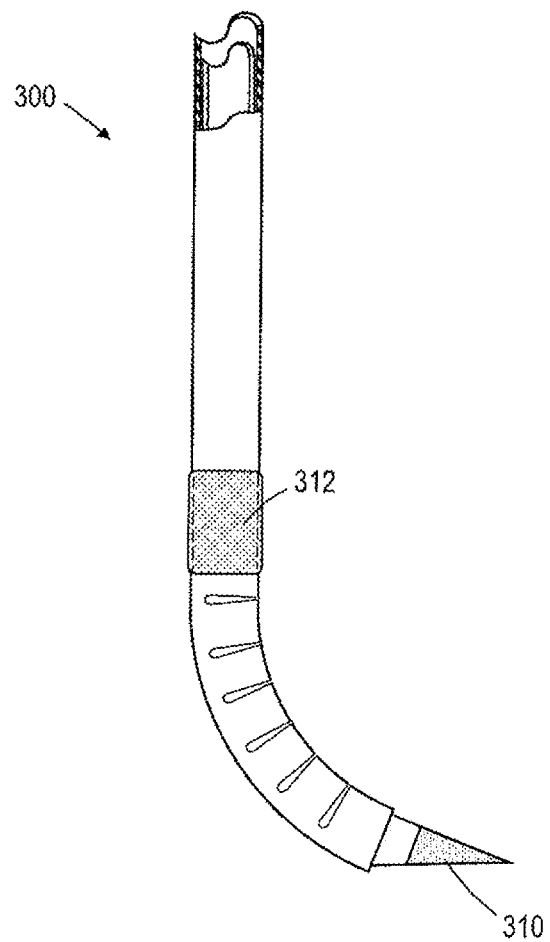
FIG. 15 illustrates a variation of an osteotome as described herein having electrodes on a tip of the device and another electrode on the shaft.

In an additional variation, the osteotome device can include one or more electrodes 310, 312 as shown in FIG. 15. In this particular example, the device 300 includes spaced apart electrodes having opposite polarity to function in a bi-polar manner. However, the device can include a monopolar configuration. Furthermore, one or more electrodes can be coupled to individual channels of a power supply so that the electrodes can be energized as needed. Any variation of the device described above can be configured with one or more electrodes as described herein.

Figure 16:
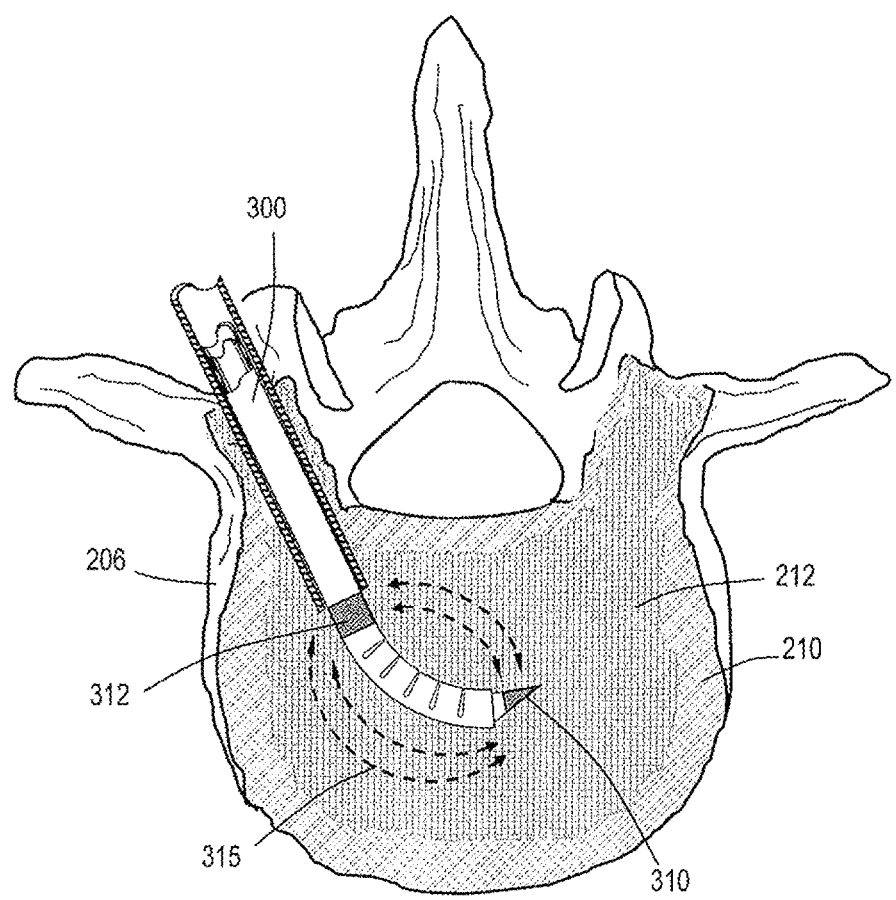
FIG. 16 illustrates an osteotome device as shown in FIG. 15 after being advanced into the body and where current passes between electrodes.

FIG. 16 illustrates an osteotome device 300 after being advanced into the body as discussed above. As shown by lines 315 representing current flow between electrodes, when required, the physician can conduct RF current between electrodes 310 and 312 to apply coagulative or ablative energy within the bone structure of the vertebral body (or other hard tissue). While FIG. 16 illustrates RF current 315 flow between electrodes 310 and 312, variations of the device can include a number of electrodes along the device to apply the proper therapeutic energy. Furthermore, an electrode can be spaced from the end of the osteotome rather than being placed on the sharp tip as shown by electrode 310. In some variations, the power supply is coupled to the inner sharp tip or other working end of the first sleeve. In those variations with only two sleeves, the second pole of the power supply is coupled with the second sleeve (that is the exterior of the device) to form a return electrode. However, in those variations having three sleeves, the power supply can alternatively be coupled with the third outer sleeve. In yet additional variations, the second and third sleeves can both function as return electrodes. However, in those devices that are monopolar, the return electrode will be placed outside of the body on a large area of skin.

FIGS. 17 to 20 illustrate another variation of an articulating probe or osteotome device 500. In this variation, the device 500 includes a working end 505 that carries one or more RF electrodes that can be used to conduct current therethrough. Accordingly, the device can be used to sense impedance of tissue, locate nerves, or simply apply electrosurgical energy to tissue to coagulate or ablate tissue. In one potential use, the device 500 can apply ablative energy to a tumor or other tissue within the vertebra as well as create a cavity.

Figure 17:
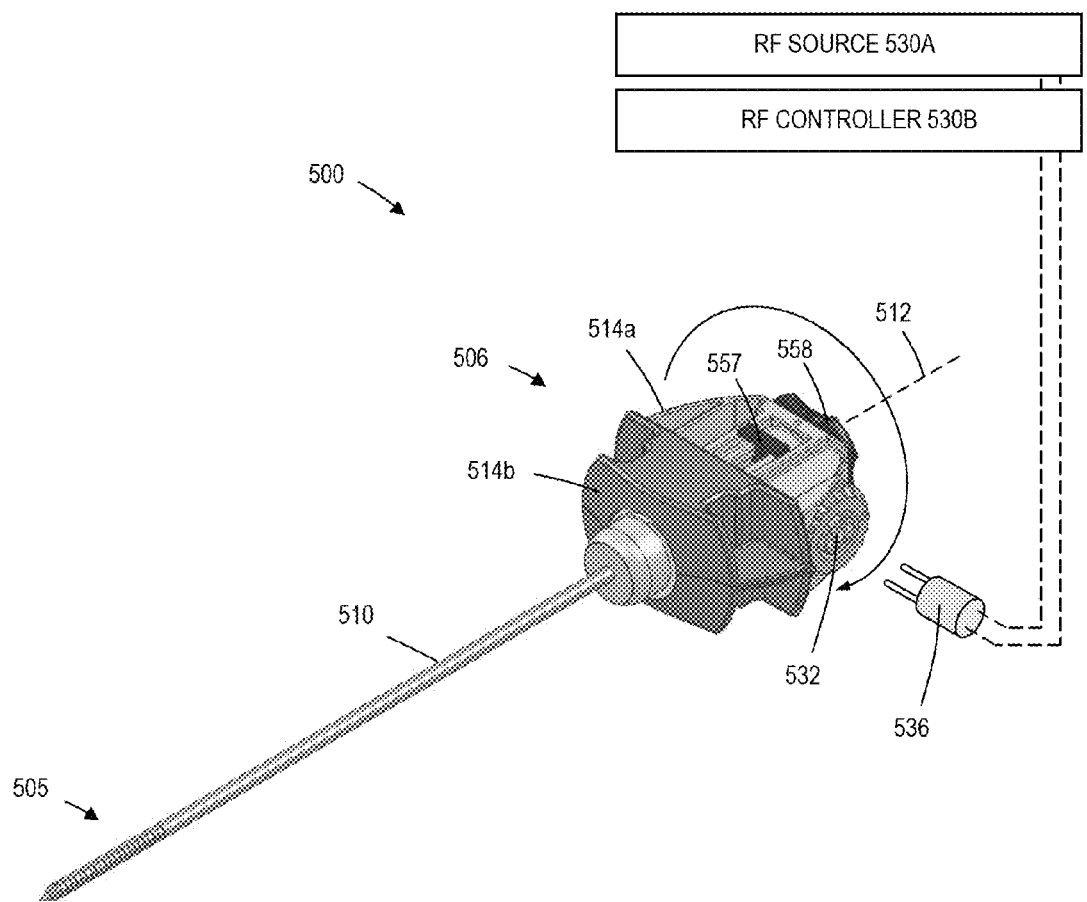
FIG. 17 illustrates a variation of a device as described herein further including a connector for providing energy at the working end of the device.
Figures 18A, 18B:
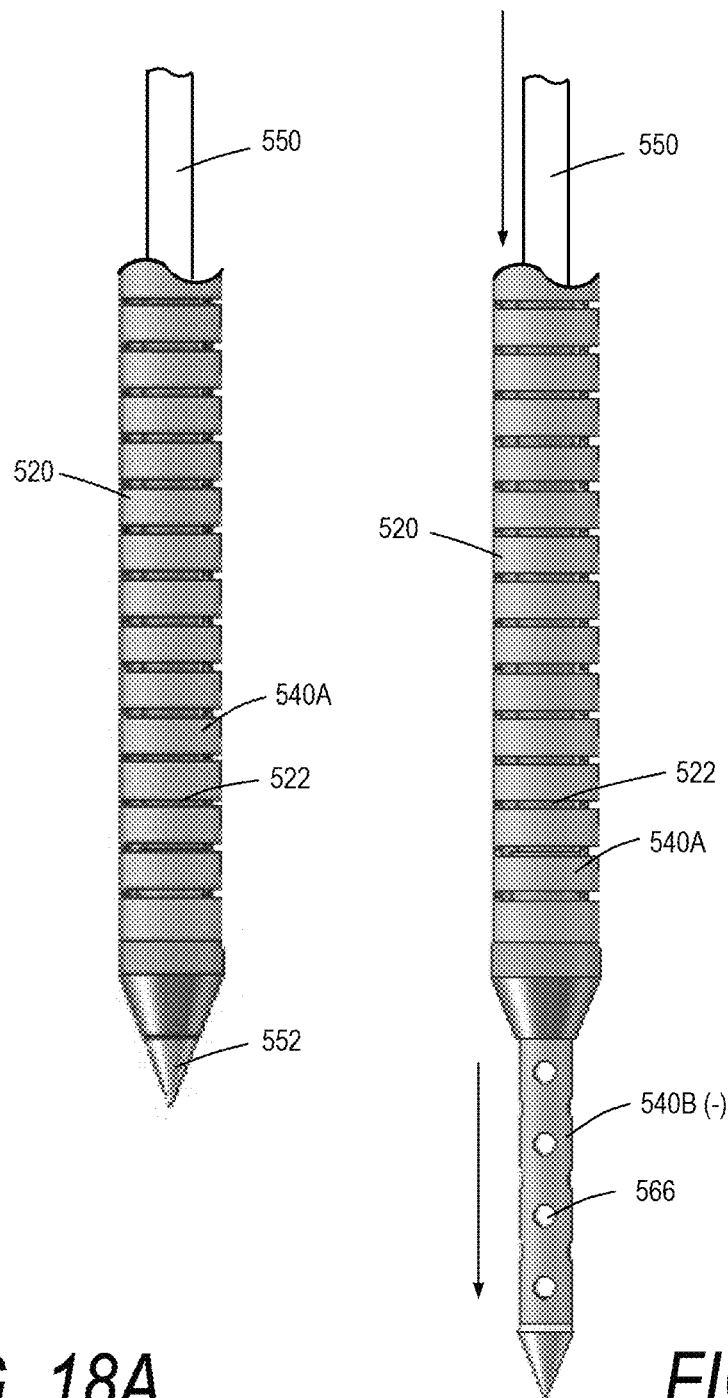
FIGS. 18A and 18B illustrate a device having a sharp tip as disclosed herein where the sharp tip is advanceable from the distal end of the shaft.
Figure 19:
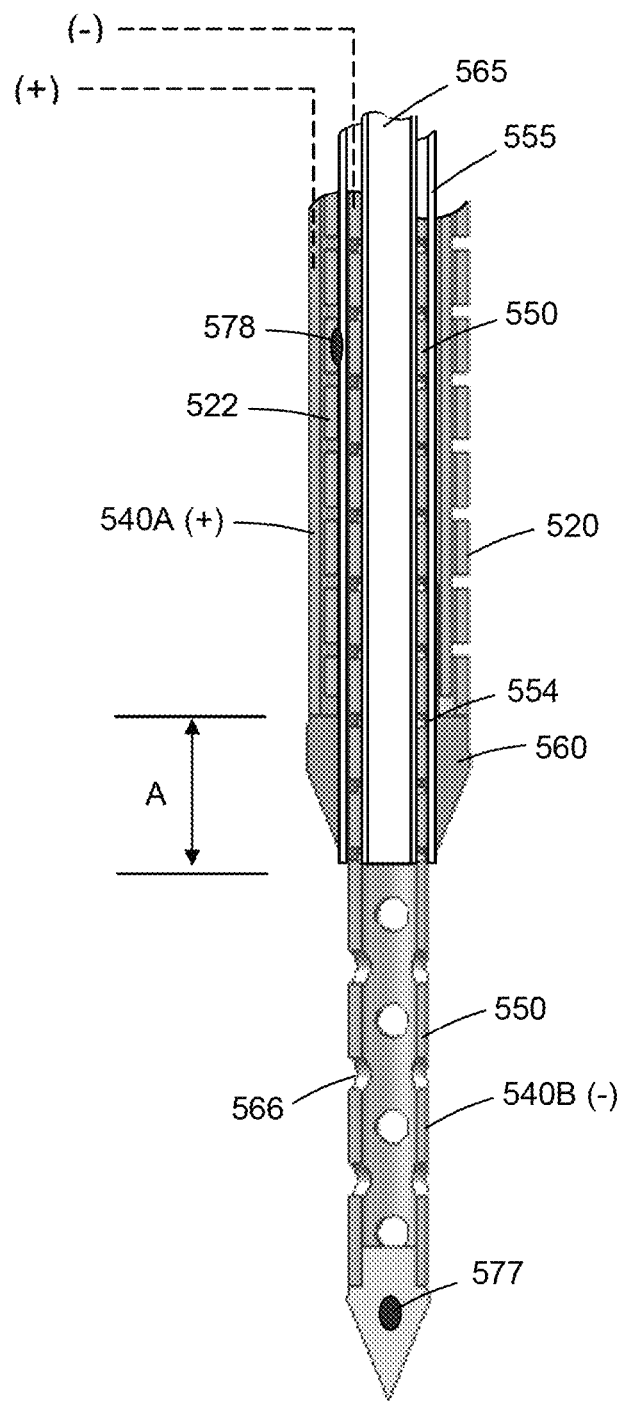
FIG. 19 shows a cross sectional view of the device illustrated in FIG. 18B and also illustrates temperature sensing elements located on device.

FIGS. 17, 18A, 18B and 19, illustrate a variation of the device 500 as having a handle portion 506 coupled to a shaft assembly 510 that extends along axis 512 to the articulating working end 505. The articulating working end 505 can be actuatable as described above. In addition, FIG. 17 shows that handle component 514a can be rotated relative to handle component 514b to cause relative axial movement between a first outer sleeve 520 and second inner sleeve 522 (FIG. 19) to cause the slotted working ends of the sleeve assembly to articulate as described above. The working end 505 of FIG. 19 shows two sleeves 520 and 522 that are actuatable to articulate the working end, but it should be appreciated that a third outer articulating sleeve can be added as depicted above. In one variation, the articulating working end can articulate 90° by rotating handle component 514a between ¼ turn and ¾ turn. The rotating handle component 514a can include detents at various rotational positions to allow for controlled hammering of the working end into bone. For example, the detents can be located at every 45° rotation or can be located at any other rotational increment.

FIG. 17 depict an RF generator 530A and RF controller 530B connectable to an electrical connector 532 in the handle component 514a with a plug connector indicated at 536. The RF generator is of the type known in the art for electrosurgical ablation. The outer sleeve 520 comprises a first polarity electrode indicated at 540A (+). However, any energy modality can be employed with the device.

FIGS. 18A and 18B illustrate yet another variation of a working end of a device for creating cavities in hard tissue. As shown, the device 500 can include a central extendable sleeve 550 with a sharp tip 552 that is axially extendable from passageway 554 of the assembly of first and second sleeves 520 and 522 (FIG. 19). The sleeve 550 can also include a second polarity electrode indicated at 540B (−). Clearly, the first and second electrodes will be electrically insulated from one another. In one variation, and as shown in FIG. 19, the sleeve assembly can carry a thin sleeve 555 or coating of an insulative polymer such as PEEK to electrically isolate the first polarity electrode 540A (+) from the second polarity electrode 540B (−). The electrode can be deployed by rotating knob 558 on the striking surface of handle component 514a (FIG. 17). The degree of extension of central sleeve 550 can optionally be indicated by a slider tab 557 on the handle. In the illustrated variation, the slider tab is located on either side of handle component 514a (FIG. 17). Sleeve 550 can be configured to extend distally beyond the assembly of sleeves 520 and 522 a distance of about 5 to 15 mm.

Referring to FIG. 19, the central extendable sleeve 550 can have a series of slots in at least a distal portion thereof to allow it to bend in cooperation with the assembly of first and second sleeves 520 and 522. In the embodiment shown in FIG. 18B, the central sleeve 550 can optionally include a distal portion that does not contain any slots. However, additional variations include slots on the distal portion of the sleeve.

FIG. 19 further depicts an electrically insulative collar 560 that extends length A to axially space apart the first polarity electrode 540A (+) from the second polarity electrode 540B (−). The axial length A can be from about 0.5 to 10 mm, and usually is from 1 to 5 mm. The collar can be a ceramic or temperature resistant polymer.

FIG. 19 also depicts a polymer sleeve 565 that extends through the lumen in the center of electrode sleeve 550. The polymer sleeve 565 can provide saline infusion or other fluids to the working end and/or be used to aspirate from the working end when in use. The distal portion of sleeve 550 can include one or more ports 566 therein for delivering fluid or aspirating from the site.

Figure 20:
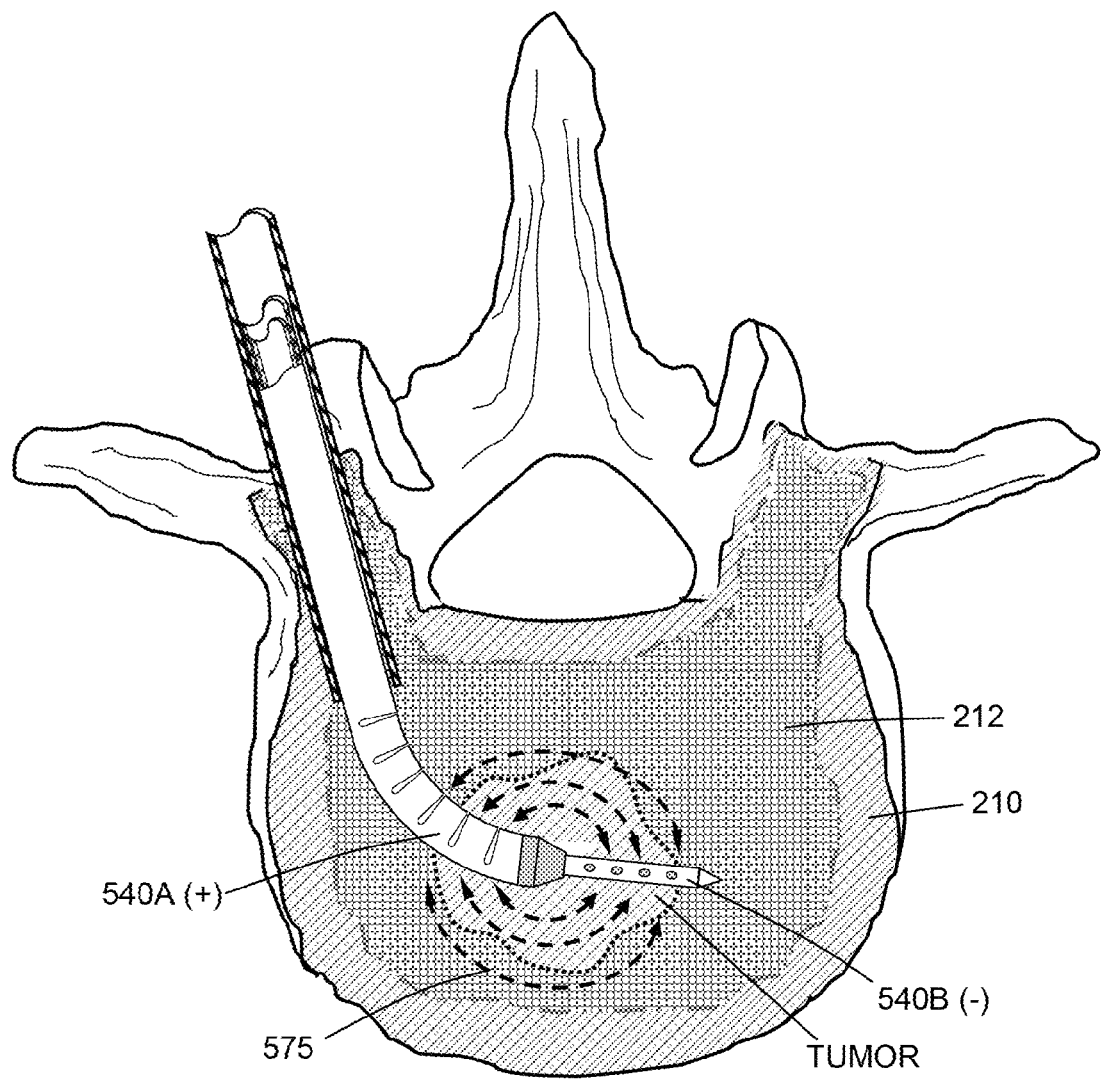
FIG. 20 shows a variation of a device where the inner sleeve is extended from the device and where current is applied between the extended portion of the inner sleeve and the shaft to treat tissue.

In all other respects, the osteotome system 500 can be driven into bone and articulated as described above. The electrodes 540A and 540B are operatively coupled to a radiofrequency generator as is known in the art for applying coagulative or ablative electrosurgical energy to tissue. In FIG. 20, it can be seen that RF current 575 is indicated in paths between electrodes 540A and 540B as shown by lines 575. RF generator 530A and controller 530B for use with the devices described herein can include any number of power settings to control the size of targeted coagulation or ablation area. For example, the RF generator and controller can have Low (5 watts), medium (15 Watts) and High (25 watts) power settings. The controller 530B can have a control algorithm that monitors the temperature of the electrodes and changes the power input in order to maintain a constant temperature. At least one temperature sensing element (e.g., a thermocouple) can be provided on various portions of the device. For example, and as shown in FIG. 19, a temperature sensing element 577 can be provided at the distal tip of sleeve 550 tip while a second temperature sensing element 578 can be provided proximal from the distal tip to provide temperature feedback to the operator to indicate the region of ablated tissue during the application of RF energy. In one example, the second temperature sensing element was located approximately 15 to 20 mm from the distal tip.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

What is claimed is:

1. A medical device for mechanically displacing hard tissue and coupleable to a power supply, the medical device comprising:
    a handle having an actuating portion and a connector for electrically coupling the device to the power supply;
    a shaft comprising a first sleeve located concentrically within a second sleeve, the shaft having a distal portion comprising a working end capable of moving between a linear configuration and an articulated configuration where the articulated configuration is limited to a single plane, and where each sleeve comprises a series of slots or notches to limit deflection of the working end to the articulated configuration, where the respective series of slots or notches are radially offset in adjacent sleeves, where a first conductive portion of the shaft is electrically coupleable to a first pole of the power supply;
    a sharp tip located at a distal tip of the first sleeve of the working end, the sharp tip adapted to penetrate bone within the tissue, where the distal tip is coupleable to a second pole of the power supply, such that when activated, current flows between a portion of the distal tip and the shaft;
    a non-conductive layer electrically isolating the first sleeve from the first conductive portion; and
    where the shaft and sharp tip have sufficient column strength such that application of an impact force on the handle causes the distal portion of the shaft and the distal tip to mechanically displace the hard tissue.

2. The medical device of claim 1, where the first sleeve is affixed to the second sleeve at the working end such that relative axial movement of the first and second sleeves causes the working end to assume the articulated configuration.

3. The medical device of claim 1, where the second sleeve is electrically coupleable to the power supply such that the first conductive portion is on the second sleeve.

4. The medical device of claim 1, further comprising a third sleeve located concentrically about the second sleeve and where the third sleeve is electrically coupleable to the power supply such that the first conductive portion is on the third sleeve.

5. The medical device of claim 4, where the third sleeve ends at an intermediate portion of the tool to limit torque or rotational forces generated by the handle mechanism.

6. The medical device of claim 4, where the third sleeve further includes slots or notches on an exterior surface of the third sleeve that faces outward from a direction of the curved configuration such that an interior surface of the curved configuration is solid.

7. The medical device of claim 6, where the at least one spring element comprises a plurality of spring elements.

8. The medical device of claim 4, where at least the series of slots or notches on the third sleeve have a uniform width.

9. The medical device of claim 4, where the series of slots or notches on the third sleeve vary in a width.

10. The medical device of claim 4, where the second sleeve is affixed to the third sleeve at the working end.

11. The medical device of claim 1, where the first sleeve is advanceable out of the shaft.

12. The medical device of claim 1, further comprising a force-limiting assembly coupled between the actuating portion and the first sleeve such that upon reaching a threshold force, the actuating portion disengages the first sleeve.

13. The medical device of claim 1, further comprising at least one spring element extending through the first sleeve, where the spring element is affixed to the shaft and causes the working end to assume the linear configuration in a relaxed state.

14. The medical device of claim 1, wherein the first sleeve is coupled to the actuation portion of the handle such that rotation of the actuation portion of the handle causes axial movement of the first sleeve to deform the working end into the articulated configuration.

15. The medical device of claim 1, further comprising a lumen extending through the shaft and working end.

16. The medical device of claim 15, where wherein the sharp tip is solid and where the lumen terminated proximal to the sharp tip.

17. The medical device of claim 15, further comprising a source of a bone cement material that is fluidly coupled to lumen the bone cement material can pass through the lumen to exit at the working end.

18. The medical device of claim 17, wherein the lumen terminates in a side opening in a wall of the shaft such that bone cement material exits proximal to the distal tip.

19. The medical device of claim 1, where the series of slots or notches on the first sleeve vary in a width.

20. The medical device of claim 1, where the first and second sleeves are prevented from rotating with respect to one another.

* * * * *